United States Patent [19]

Maracas et al.

[11] Patent Number: 5,731,152
[45] Date of Patent: Mar. 24, 1998

[54] METHODS AND SYSTEMS FOR BIOLOGICAL REAGENT PLACEMENT

[75] Inventors: George N. Maracas, Phoenix, Ariz.; Donald E. Ackley, Lambertville, N.J.; William L. Reber, Schaumburg, Ill.; Thomas B. Harvey, III, Scottsdale, Ariz.

[73] Assignee: Motorola, Inc., Schaumburg, Ill.

[21] Appl. No.: 648,635

[22] Filed: May 13, 1996

[51] Int. Cl.$^6$ .............. C12Q 1/68; C12Q 1/70; G01N 33/53; C12P 19/34

[52] U.S. Cl. .............. 435/6; 435/5; 435/7.1; 435/7.2; 435/7.9; 435/30; 435/287; 435/91.1; 435/91.2; 422/131; 436/500; 536/22.1; 530/334; 530/333

[58] Field of Search ............ 435/6, 5, 7.1–7.9, 435/30, 287, 91.1, 91.2; 422/131; 536/22.1; 530/334, 333; 436/500

[56] References Cited

U.S. PATENT DOCUMENTS

| | | | |
|---|---|---|---|
| 4,981,783 | 1/1991 | Augenlicht | 435/6 |
| 5,011,779 | 4/1991 | Maimon et al. | 435/293 |
| 5,061,621 | 10/1991 | Perlman | 435/30 |
| 5,324,633 | 6/1994 | Fodor et al. | 435/6 |
| 5,352,651 | 10/1994 | Debe et al. | 503/227 |
| 5,424,186 | 6/1995 | Fodor et al. | 435/6 |
| 5,449,754 | 9/1995 | Nishioka | 530/334 |
| 5,462,743 | 10/1995 | Turner et al. | 424/448 |
| 5,472,672 | 12/1995 | Brennan | 422/131 |
| 5,489,678 | 2/1996 | Fodor et al. | 536/22.1 |
| 5,503,980 | 4/1996 | Cantor | 435/6 |
| 5,512,131 | 4/1996 | Kumar et al. | 156/655.1 |
| 5,527,681 | 6/1996 | Holmes | 435/6 |
| 5,529,756 | 6/1996 | Brennan | 422/131 |
| 5,545,531 | 8/1996 | Rava et al. | 435/6 |
| 5,547,839 | 8/1996 | Dower et al. | 435/6 |
| 5,571,639 | 11/1996 | Hubbell et al. | 430/5 |
| 5,599,695 | 2/1997 | Pease et al. | 435/91.1 |

OTHER PUBLICATIONS

Sommer and Tautz, "Minimal Homology Requirements for PCR Primers", Nucleic Acids Research, vol. 17, No. 16, p. 6749, 1989.

Smith et al. Nucleic Acids Research 23: 10 1830–1831 (of interest), 1995.

Klebe et al. Somatic Cell Genetics 7:271–280, 1981.

*Primary Examiner*—W. Gary Jones
*Assistant Examiner*—Dianne Rees
*Attorney, Agent, or Firm*—Bruce E. Stuckman; Jeff G. Toler

[57] ABSTRACT

An apparatus for placing at least one biological reagent at a plurality of locations on a substrate includes a stamp member onto which the at least one biological reagent is applied. The stamp member defines a plurality of transfer elements patterned to correspond to the plurality of locations. The stamp member contacts the substrate to transfer the at least one biological reagent from the plurality of transfer elements to the plurality of locations. The transfer elements can be defined by reservoirs or projected portions of the stamp member. A method of using said apparatus is also disclosed.

44 Claims, 8 Drawing Sheets

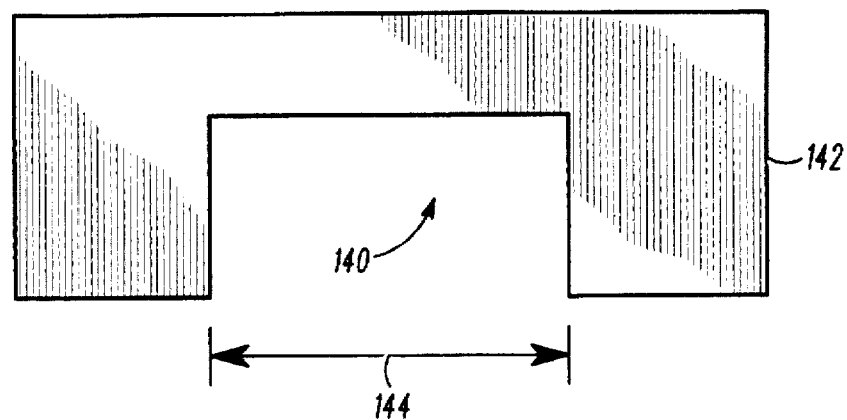
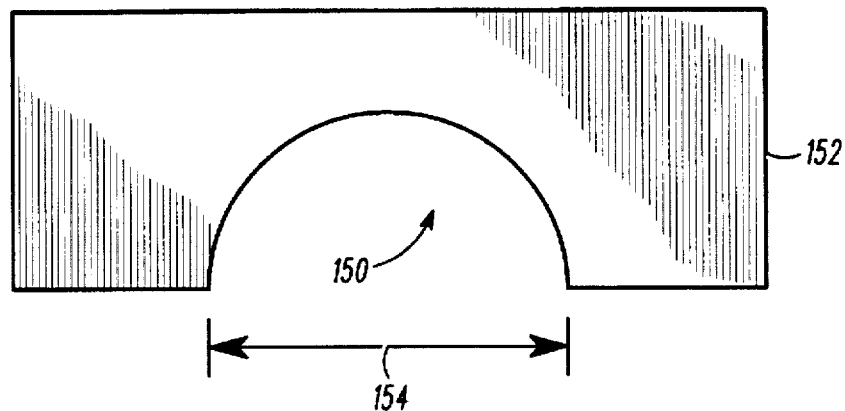
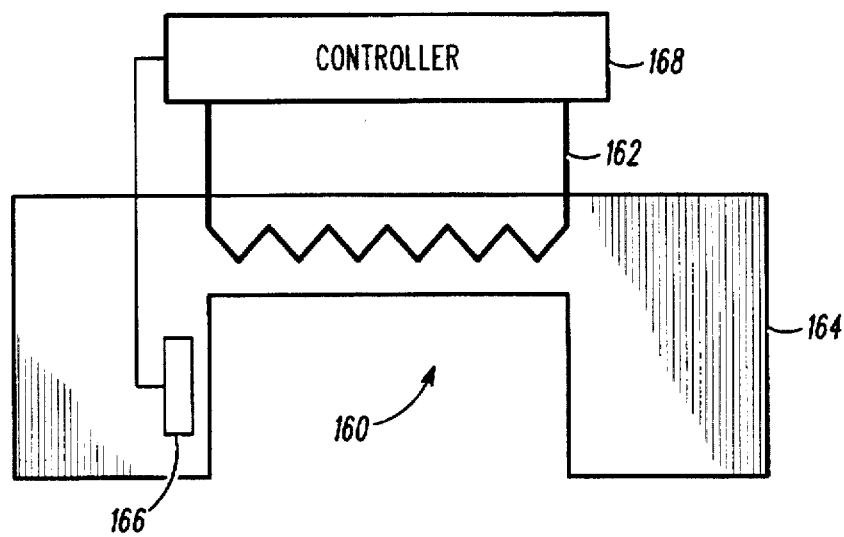

METHODS AND SYSTEMS FOR BIOLOGICAL REAGENT PLACEMENT

FIELD OF THE INVENTION

The present invention relates to methods and systems for placing biological reagents on a substrate.

BACKGROUND OF THE INVENTION

Recently, an increased effort has been directed toward the development of chips for molecular detection. In general, a molecular detection chip includes a substrate on which an array of binding sites is arranged. Each binding site (or hybridization site) has a respective molecular receptor which binds or hybridizes with a molecule having a predetermined structure. A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

A number of approaches have been devised for putting an array of molecular receptors on a substrate. Affymax has proposed a lithographic technique of synthesizing peptides or nucleic acids on a glass surface. To synthesize an array of n-mer oligonucleotide probes, 4 n lithographic write steps are required. This results from the four different constituent nucleotides (adenine, cytosine, guanine, and thymine) which can be located at each of the n nucleotide locations in an n-mer probe. A shortcoming of the lithographic technique is that a new set of lithographic masks must be produced if a new configuration of probes is desired in the array. Further, the use of 4 n mask levels results in an undesirably low yield.

Currently, a molecular sample is applied to probes on a molecular detection chip by immersing the chip into a sample solution. This approach requires a relatively large quantity of samples whose quantity is often limited. Further, molecules will often bind erroneously to sites on the molecular detection chip to produce false positive readings.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

FIG. 4 is an illustration of a rectangular-shaped reservoir for use as a transfer element;

FIG. 5 is an illustration of a spherical-shaped reservoir for use as a transfer element;

FIG. 6 is an illustration of a means for controlling a temperature in a reservoir;

DETAILED DESCRIPTION OF A PREFERRED EMBODIMENT

Figure 1:
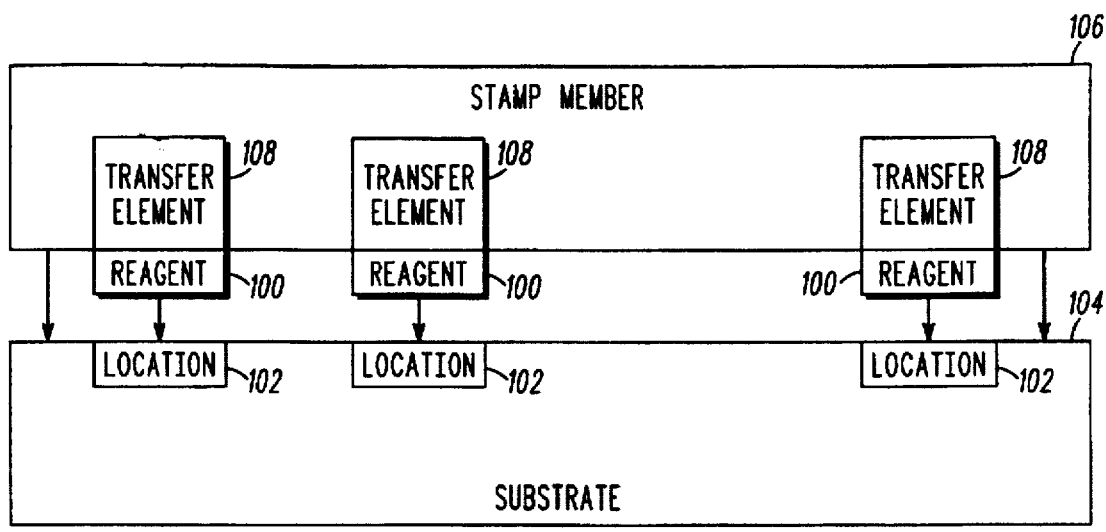
FIG. 1 is a block diagram of an embodiment of an apparatus for placing at least one biological reagent at a plurality of locations on a substrate.

FIG. 1 is a block diagram of an embodiment of an apparatus for placing at least one biological reagent 100 at a plurality of locations 102 on a substrate 104. The apparatus includes a stamp member 106 onto which the at least one biological reagent 100 is applied. The stamp member 106 defines a plurality of transfer elements 108 patterned to correspond to the plurality of locations 102. The at least one biological reagent 100 is transferred from the plurality of transfer elements 108 to the plurality of locations 102 by contacting the stamp member 106 with the substrate 104.

The at least one biological reagent 100 can include a common biological reagent which is applied to each of the plurality of transfer elements 108. In this case, the common biological reagent is transferred to all of the plurality of locations 102 on the substrate 104, and hence, is common to all of the plurality of locations 102. Alternatively, each of the plurality of transfer elements 108 can receive a respective one of the at least one biological reagent 100. Here, different biological reagents can be transferred to different locations on the substrate 104.

It is noted that the at least one biological reagent 100, in this embodiment and other embodiments described herein, can generally comprise any reagent or chemical. Of particular interest, however, are biological reagents including, but not limited to, single nucleotides, nucleotide chains such as DNA fragments and RNA fragments, and other nucleic acids.

Embodiments of the present invention can be advantageously utilized for transferring biological reagents to a substrate which forms a molecular detection apparatus, such as a gene sequencing chip or a disease diagnosis chip. The biological reagents can be transferred to form molecular detection probes at binding sites of the molecular detection apparatus. Alternatively, the biological reagents can include target molecules which hybridize with selective ones of the binding sites already having molecular detection probes.

It is also noted that the substrate 104 can be formed of a variety of materials which include, but are not limited to, metals, semiconductors, paper, glass, and plastic, for the various embodiments of the present invention described herein. The substrate 104 can be either flexible or rigid, and can have any shape, including but not limited to a planar shape, a roll shape, and a cylindrical shape.

Figure 2:
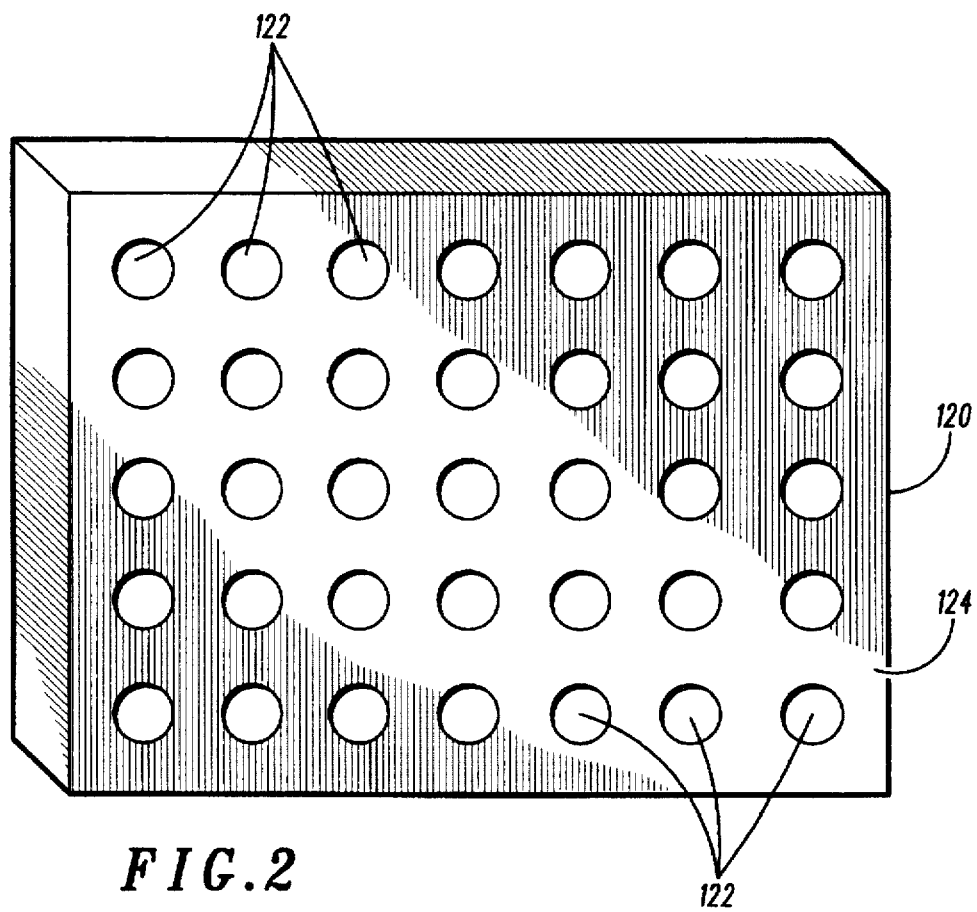
FIG. 2 is an illustration of an embodiment of a stamp member in accordance with the present invention.

FIG. 2 is an illustration of an embodiment of a stamp member 120 in accordance with the present invention. The stamp member 120 defines a plurality of transfer elements 122. The plurality of transfer elements 122 can be patterned as an array, such as the two-dimensional array illustrated in FIG. 2, to correspond to an array of locations on a substrate. It is noted, however, that alternative patterns of the plurality of transfer elements 122 can be utilized. The stamp member 120 has a face 124 at which the plurality of transfer elements 122 is defined. In this embodiment, the face 124 is substantially planar.

Figure 3:
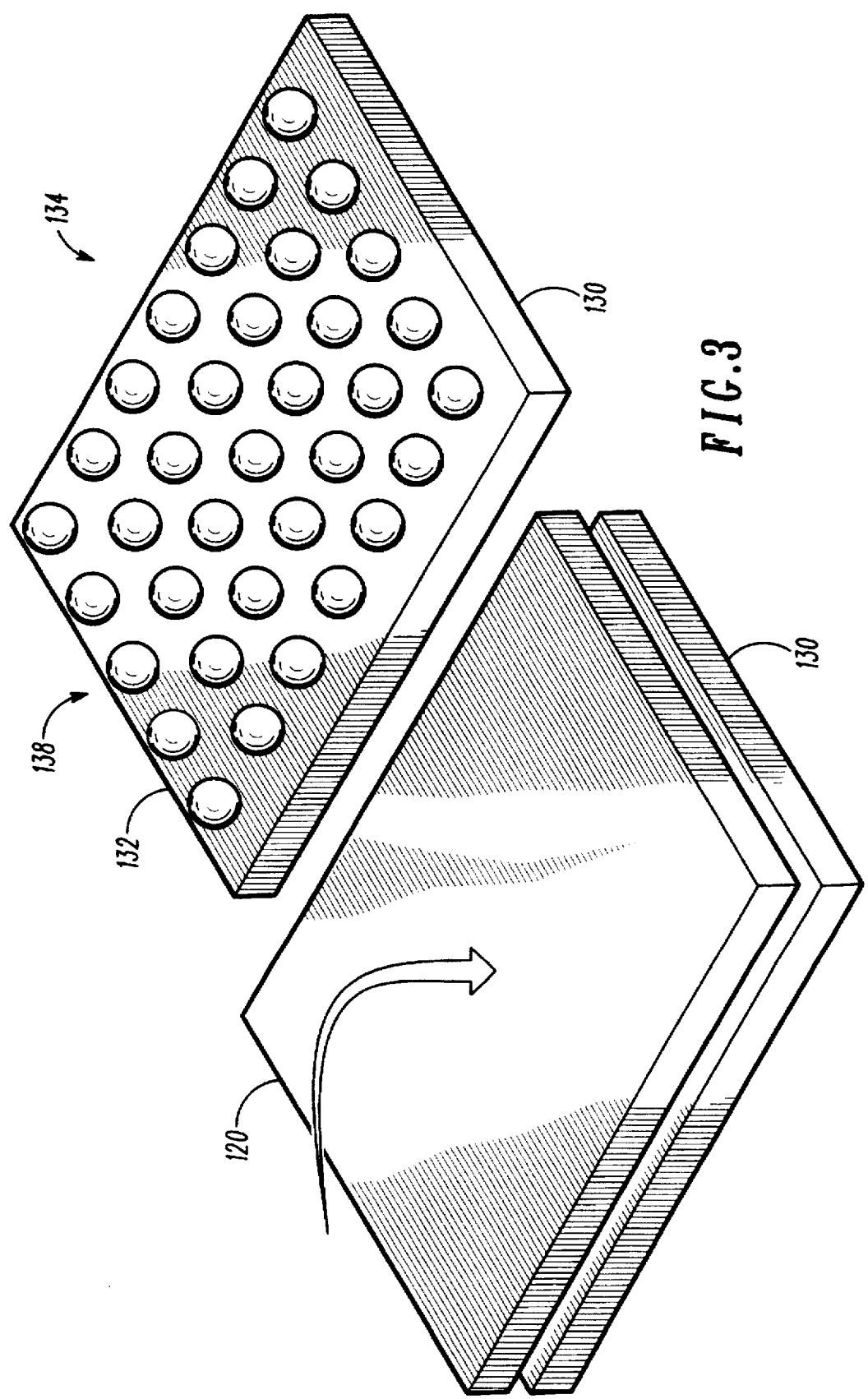
FIG. 3 illustrates at least one biological reagent being transferred to a substrate from the stamp member of FIG. 2.

FIG. 3 illustrates at least one biological reagent being transferred to a substrate 130 from the stamp member 120 of FIG. 2. The face 124 of the stamp member 120 is directed toward a surface 132 of the substrate 130 until contact is made. At contact, either the face 124 contacts the substrate 130, or at least one of the plurality of transfer elements 122 contacts the substrate 130. Thereafter, as indicated by reference numeral 134, the stamp member 120 is removed from the substrate 130. Here, either the at least one biological reagent or a reaction product thereof remains at a plurality of locations 138 of the substrate 130.

In the various embodiments of the present invention, the plurality of transfer elements can have any of a variety of forms. In one form, the plurality of transfer elements includes a plurality of reservoirs defined on a surface of the stamp member. The plurality of reservoirs are arranged to correspond to the plurality of locations on the substrate. Each reservoir has the form of a small inclusion in the stamp member for holding small quantities of reagents for chemical reactions. For example, the reservoirs can be utilized to contain on the order of a picoliter of a reagent.

Using conventional aligning techniques for mask/wafer positioning, at least one reagent can be accurately placed at predetermined locations of a chemically-sensitive substrate by contacting the substrate with a stamp member having a corresponding array of reservoirs. While the stamp member is in contact with the substrate, any chemical reactions between the at least one reagent and the chemically-sensitive substrate are contained within the reservoirs. Preferably, the reservoirs have a predetermined shape and a predetermined volume so as not to significantly affect the chemical reaction of interest.

The stamp member is held in contact with the substrate until the chemical reactions have completed. Thereafter, the stamp member is removed from the substrate leaving regions of reaction products on the substrate.

FIG. 4 is an illustration of a rectangular-shaped reservoir 140 for use as a transfer element. The rectangular-shaped reservoir 140 is defined within a portion of a stamp member 142. In one embodiment, the rectangular-shaped reservoir 140 has a dimension 144 greater than 10 µm so as not to affect a predetermined chemical reaction performed therein.

FIG. 5 is an illustration of a spherical-shaped reservoir 150 for use as a transfer element. The spherical-shaped reservoir 150 is defined within a portion of a stamp member 152. Similar to the rectangular-shaped reservoir 140, the spherical-shaped reservoir 150 can have a diameter 154 greater than 10 µm so as not to affect a predetermined chemical reaction performed therein.

FIG. 6 is an illustration of a means for controlling a temperature in a reservoir 160. A heating element 162 is embedded in a stamp member 164 proximate to the reservoir 160. The heating element 162 can be a resistive heating element, for example, which heats the reservoir 160 in dependence upon a current applied therethrough.

A temperature probe 166 is embedded in the stamp member 164 proximate to the reservoir 160. The temperature probe 166 measures the temperature of the reservoir 160 or of a reagent in the reservoir 160. A signal representative of the temperature is communicated from the temperature probe 166 to a controller 168. The controller 168 processes the signal to form a control signal which is applied to the heating element 162. The control signal is formed in order to control the temperature to a desired level.

By embedding a heating element and a temperature probe in each of a plurality of reservoirs, the temperature at each reservoir can be locally controlled. This is useful for controlling hybridization of genetic material onto specific substrate locations for diagnostic purposes.

Temperature control at a reservoir is also beneficial for providing a means for amplifying a biological sample contained therein. Here, the temperature can be controlled to provide the heating steps in a PCR (polymerase chain reaction) amplification technique.

For the various embodiments of the present invention described herein, the at least one biological reagent can be introduced into the reservoirs by a number of different techniques. One technique is to provide a substantially uniform wetting of the stamp member. Here, the stamp member can be immersed in a fluid containing the at least one reagent to fill each of the reservoirs. Alternatively, the face of the stamp member can be rolled on or contacted with a saturated absorbent material containing the at least one reagent. In both of these cases, the same at least one reagent is typically applied to all of the reservoirs.

Figure 7:
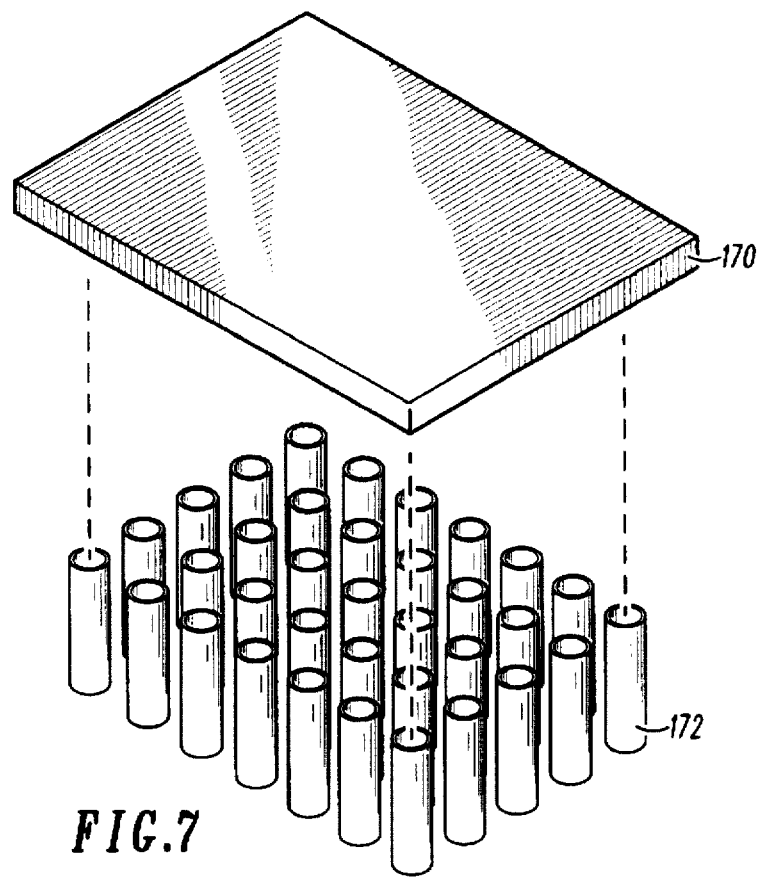
FIG. 7 is an illustration of another technique to introduce the at least one reagent into the reservoirs.

FIG. 7 is an illustration of another technique to introduce the at least one reagent into the reservoirs. Here, the at least one reagent is directly placed into a plurality of reservoirs of a stamp member 170 using a corresponding plurality of capillaries 172 (or a corresponding plurality of micropipets). As illustrated, the at least one reagent can be applied to the reservoirs from the bottom of the stamp member 170.

Figure 8:
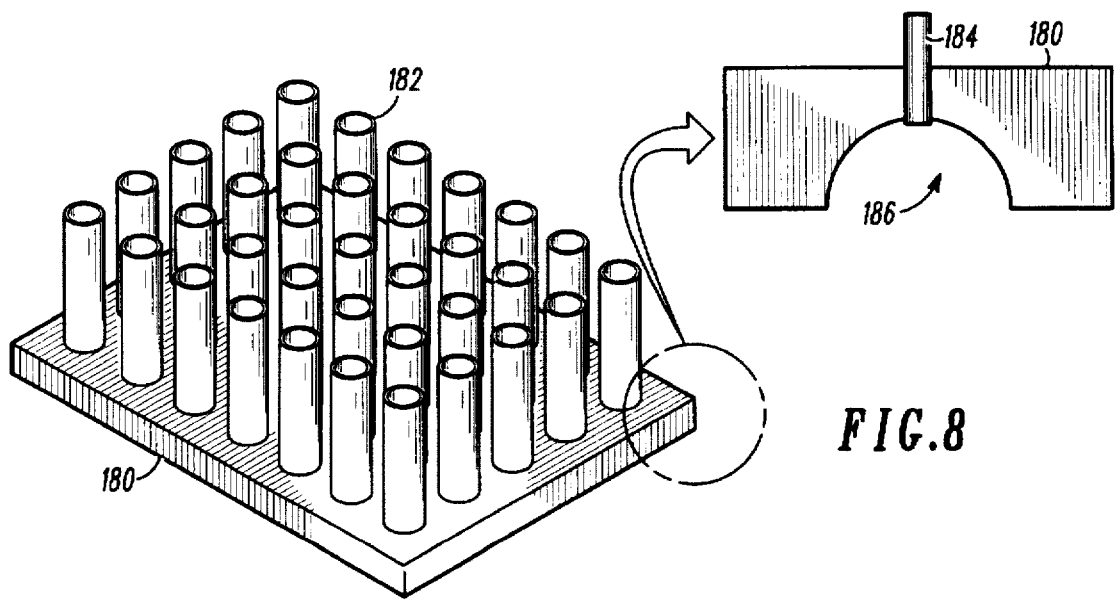
FIG. 8 is an illustration of an embodiment of a stamp member which provides another technique for applying the at least one reagent into the reservoirs.

FIG. 8 is an illustration of an embodiment of a stamp member 180 which provides another technique for applying the at least one reagent into the reservoirs. A plurality of capillaries 182 or other like tube members is embedded in the stamp member 180. A capillary 184 of the plurality of capillaries 182 is illustrated in more detail. The capillary 184 is embedded in the stamp member 180 proximate to a reservoir 186. The capillary 184 provides fluidic communication to the reservoir 186. Using this embodiment, a respective biological reagent can be applied to each of the plurality of reservoirs by a respective one of the plurality of capillaries 182.

The direct placement approaches illustrated in FIGS. 7 and 8 are advantageous over the uniform wetting approaches with respect to both reagent quantity and placement. Specifically, a reduced amount of reagent is needed to fill the reservoirs using direct placement. Further, different reagents can be applied to different reservoirs for placement at different locations on the substrate.

As described earlier, the plurality of transfer elements in accordance with the present invention can have any of a variety of forms. A second form for the transfer elements is illustrated in FIG. 9.

Figure 9:
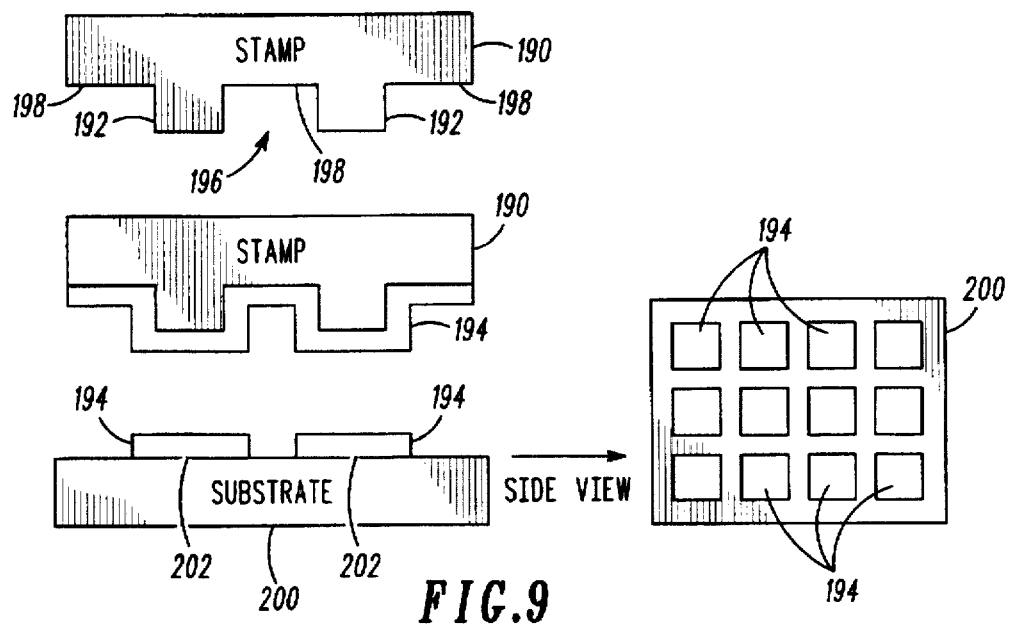
FIG. 9 is an illustration of a stamp member having a plurality of projected portions which define a plurality of transfer elements.

FIG. 9 is an illustration of a stamp member 190 having a plurality of projected portions 192 which define a plurality of transfer elements. The plurality of projected portions 192 are patterned to correspond to a plurality of locations on a substrate at which one or more reagents are to be placed.

The plurality of projected portions 192 absorb at least one biological reagent 194 which is applied to a face 196 of the stamp member 190. As illustrated, the at least one biological reagent 194 can also be absorbed by non-projected portions 198 of the stamp member 190. This can occur if the at least one biological reagent 194 is applied using a uniform wetting technique as described earlier.

The stamp member 190 is contacted with a substrate 200 to transfer the at least one biological reagent 194 to a plurality of locations 202. At contact, a stamping surface 204 of each of the plurality of projected portions 192 is in contact with the substrate 200 at a respective one of the plurality of locations 202. However, the non-projected portions 198 do not contact the substrate 200. Upon removing the stamp member 190 from the substrate 200, the at least one biological reagent 194 remains at the plurality of locations 202 on the substrate 200.

The stamp member 190 can take the form of a patterned rigid or semi-rigid plate fabricated from materials which include, but are not limited to, glass, elastomer, metal, sol-gels, plastic, and polymers. One or more of these materials can be combined in the stamp member 190 to obtain a flexibility, rigidity, opacity, thermal conductivity, and/or chemical absorbency which is desired.

Figure 10:
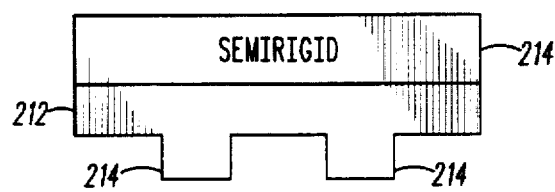
FIG. 10 illustrates an embodiment of the stamp member having a support member which supports an absorbent layer.

FIG. 10 illustrates an embodiment of the stamp member 190 having a support member 210 which supports an absorbent layer 212. The support member 210 is formed of a rigid or semi-rigid material, such as those aforementioned. The absorbent layer 212 is comprised of an absorbent material such as a sol-gel. The absorbent layer 212 defines a plurality of projected portions 214 patterned to correspond to a plurality of locations on a substrate.

Figure 11:
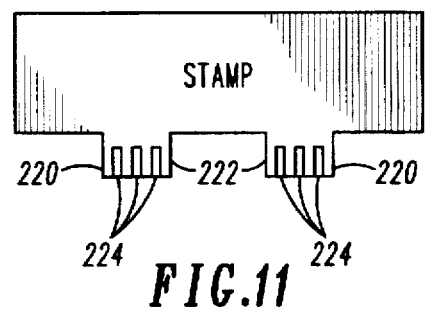
FIG. 11 illustrates an alternative approach to increasing an absorbency of the stamp member by increasing a surface area of a stamping surface.

FIG. 11 illustrates an alternative approach to increasing an absorbency of the stamp member 190 by increasing a surface area of a stamping surface. The stamp member 190 defines a plurality of projected portions 220. Each of the plurality of projected portions 220 has a stamping surface 222 which defines at least one cavity 224. The at least one cavity 224 increases the absorbency of each of the plurality of projected portions 220 by increasing a surface area of the stamping surface 222. The at least one cavity 224 can be defined by a series of ridges at each of the plurality of projected portions 220.

Figure 12:
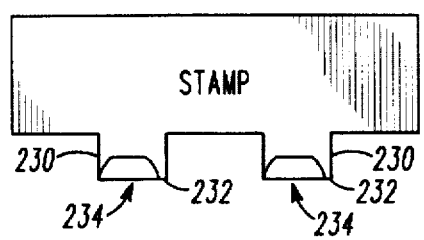
FIG. 12 illustrates an embodiment the stamp member which utilizes both projected portions and reservoirs.

FIG. 12 illustrates an embodiment the stamp member 190 which utilizes both projected portions and reservoirs. Here, each of a plurality of projected portions 230 has a stamping surface 232 which defines a reservoir 234. Each reservoir 234 is formed in accordance with any of the reservoir embodiments described herein.

As a result, each reservoir 234 can contain an accurately controlled amount of reagent which is to be transferred to a substrate. Further, a capillary can be embedded in the stamp member 190 to apply a biological reagent to the reservoir 234 of at least one of the plurality of projected portions 230. Also, a heating element and a temperature probe can be embedded in the stamp member 190 proximate to the reservoir 234 to provide temperature control means for at least one of the projected portions 230. The temperature control means can be utilized to provide a means for amplifying a biological sample within the reservoir 234 of at least one of the plurality of projected portions 230.

The projected portions in the above-described embodiments of stamp members can be either fixed or selectively projected. Various means for selectively projecting at least one of the plurality of projected portions can be utilized to allow a single stamp member to be reconfigured for a different pattern of locations on a substrate.

Figure 13:
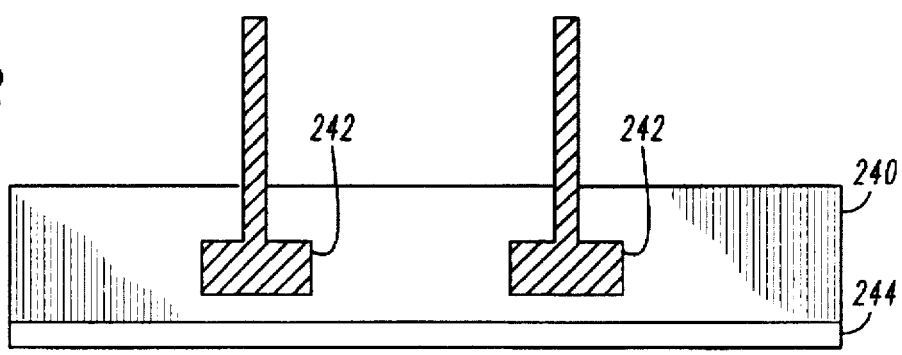
FIG. 13 illustrates an embodiment of a stamp member having selectively projectable transfer elements.

FIG. 13 illustrates an embodiment of a stamp member 240 having selectively projectable transfer elements. A plurality of pistons 242 or other like translational mechanisms are included in the stamp member 240. Each of the plurality of pistons 242 is independently projectable to form a respective projected portion. Preferably, each of the plurality of pistons 242 is electromechanically projectable. As a result, a pattern of transfer elements for the stamp member 240 is electronically programmable based upon a plurality of electrical signals.

Selected ones of the plurality of pistons 242 are projected to form a pattern of transfer elements. An absorbent layer 244 is deformed by the selected pistons which are projected. The absorbent layer 244 is utilized to receive a biological reagent for transfer to a substrate. This approach can be utilized for defining patterns having dimensions of hundreds of microns, including dimensions as small as 100 µm and below. The use of selectively projectable transfer elements is advantageous in reducing a number of stamps required for a multilevel process.

Figure 14:
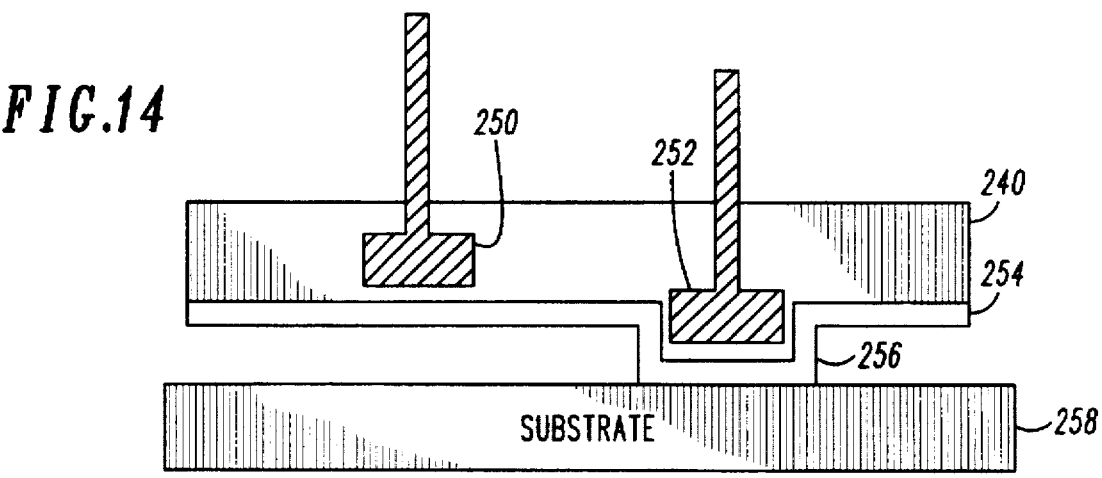
FIG. 14 illustrates the stamp member having an unprojected piston and a projected piston.

FIG. 14 illustrates the stamp member 240 having an unprojected piston 250 and a projected piston 252. The projected piston 252 deforms an absorbent layer 254 to form a projected portion 256. The projected portion 256 causes a biological reagent to be transferred to a corresponding location on a substrate 258 which contacts the stamp member 240.

Figure 15:
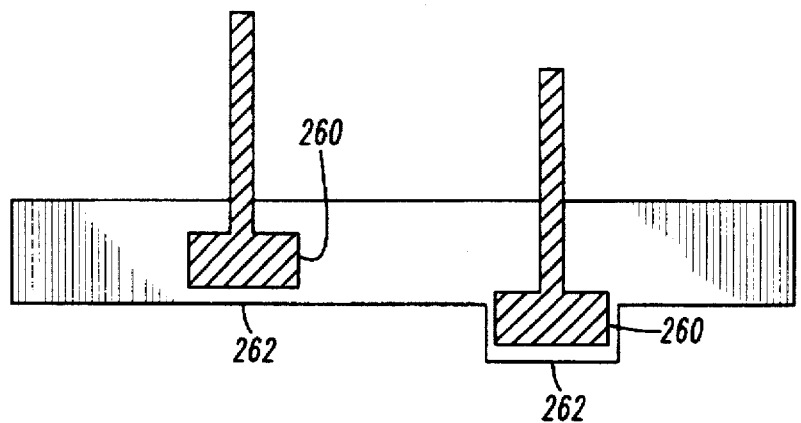
FIG. 15 illustrates an embodiment of a selectively projectable stamp member having means for temperature control.

FIG. 15 illustrates an embodiment of a selectively projectable stamp member having means for temperature control. Here, each of a plurality of pistons 260 has a heating element 262 mounted thereto. Optionally, a temperature probe (not specifically illustrated) can also be mounted to each of the plurality of pistons 260. The heating element 262 allows the temperature of each of the projected portions to be controlled for purposes described earlier.

In various embodiments of the present invention, the stamp member can have various shapes including, but not limited to, a planar shape, a cylindrical shape, a spherical shape, and other curved shapes. The cylindrical shape is advantageous in that the stamp member can be rolled onto the substrate to transfer the at least one biological reagent from the plurality of transfer elements to the plurality of locations.

Figure 16:
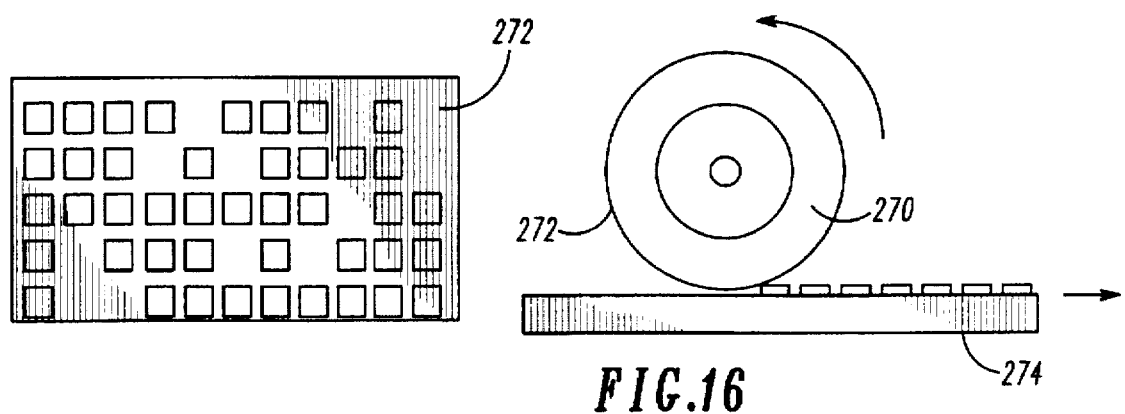
FIG. 16 shows an example of a stamp member having a cylindrical shape.

FIG. 16 shows an example of a stamp member 270 having a cylindrical shape. An outer circumferential surface 272 of the stamp member 270 defines a plurality of transfer elements patterned to correspond to a plurality of locations on a substrate 274. Rolling the stamp member 270 onto the substrate 274 causes a continuous pattern of a reagent to be transferred thereto.

Figure 17:
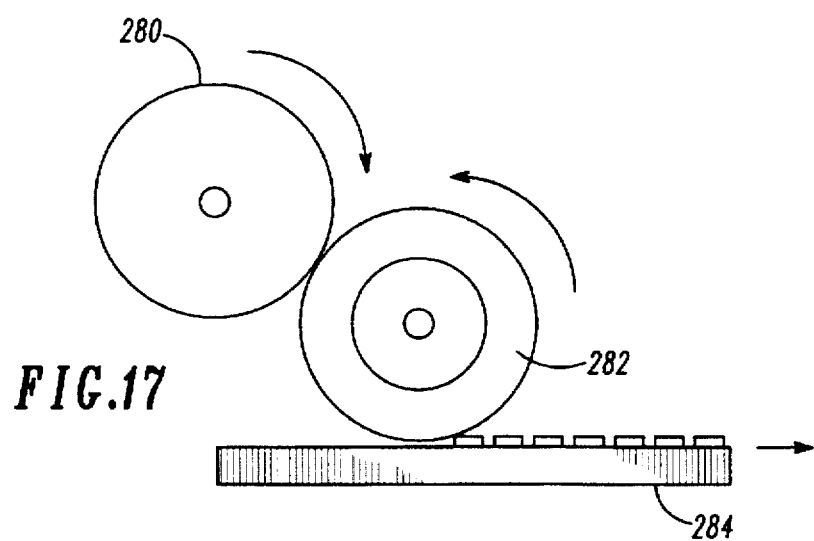
FIG. 17 illustrates a roller used to apply a reagent to a stamp member.

FIG. 17 illustrates a roller 280 used to apply a reagent to a stamp member 282. The roller 280 is well-suited for applying a single type of reagent to all of the plurality of transfer elements on the stamp member 282. Use of the roller 280 is also advantageous to simultaneously apply the reagent to a portion of the stamp member 282 while another portion of the stamp member 282 is transferring the reagent to a substrate 284. Although the stamp member 282 is illustrated to have a cylindrical shape, it is noted that a roller can be utilized to apply a reagent to stamp members having a planar shape or another shape.

Figure 18:
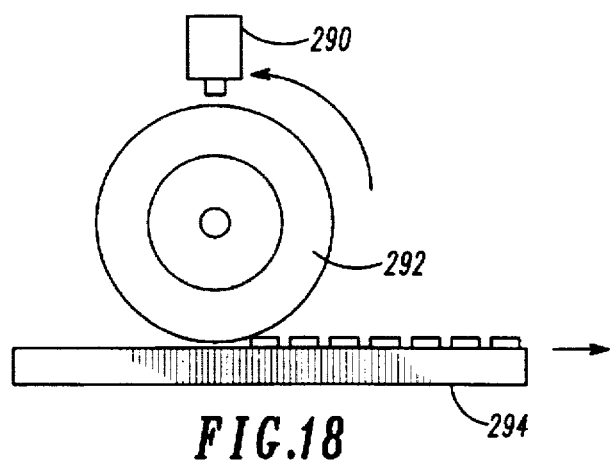
FIG. 18 illustrates at least one-dispensing head used to apply a reagent to a stamp member.

FIG. 18 illustrates at least one dispensing head 290 used to apply a reagent to a stamp member 292. The at least one dispensing head 290 applies a specific amount of the reagent directly to the plurality of transfer elements on the stamp member 292. The at least one dispensing head 290 is well-suited for applying different reagents to different transfer elements on the stamp member 292. As with the roller 280, the use of the at least one dispensing head 290 is advantageous to simultaneously apply the reagent to a portion of the stamp member 292 while another portion of the stamp member 292 is transferring the reagent to a substrate 294.

In a preferred embodiment, the at least one dispensing head 290 is included within a plurality of dispensing bars as described in the copending application entitled "Method and System for Synthesizing Oligonucleotides using Nucleotide-Specific Dispensing Bars" which is incorporated by reference into the disclosure of the present invention. Each of the plurality of dispensing bars is dedicated to dispensing a respective type of reagent. For example, each of four dispensing bars can be dedicated for applying a respective one type of four nucleotide types. Each of the plurality of dispensing bars has a plurality of individually addressable dispensing heads to dispense a reagent in any of a row of transfer elements on the stamp member 292.

Figure 19:
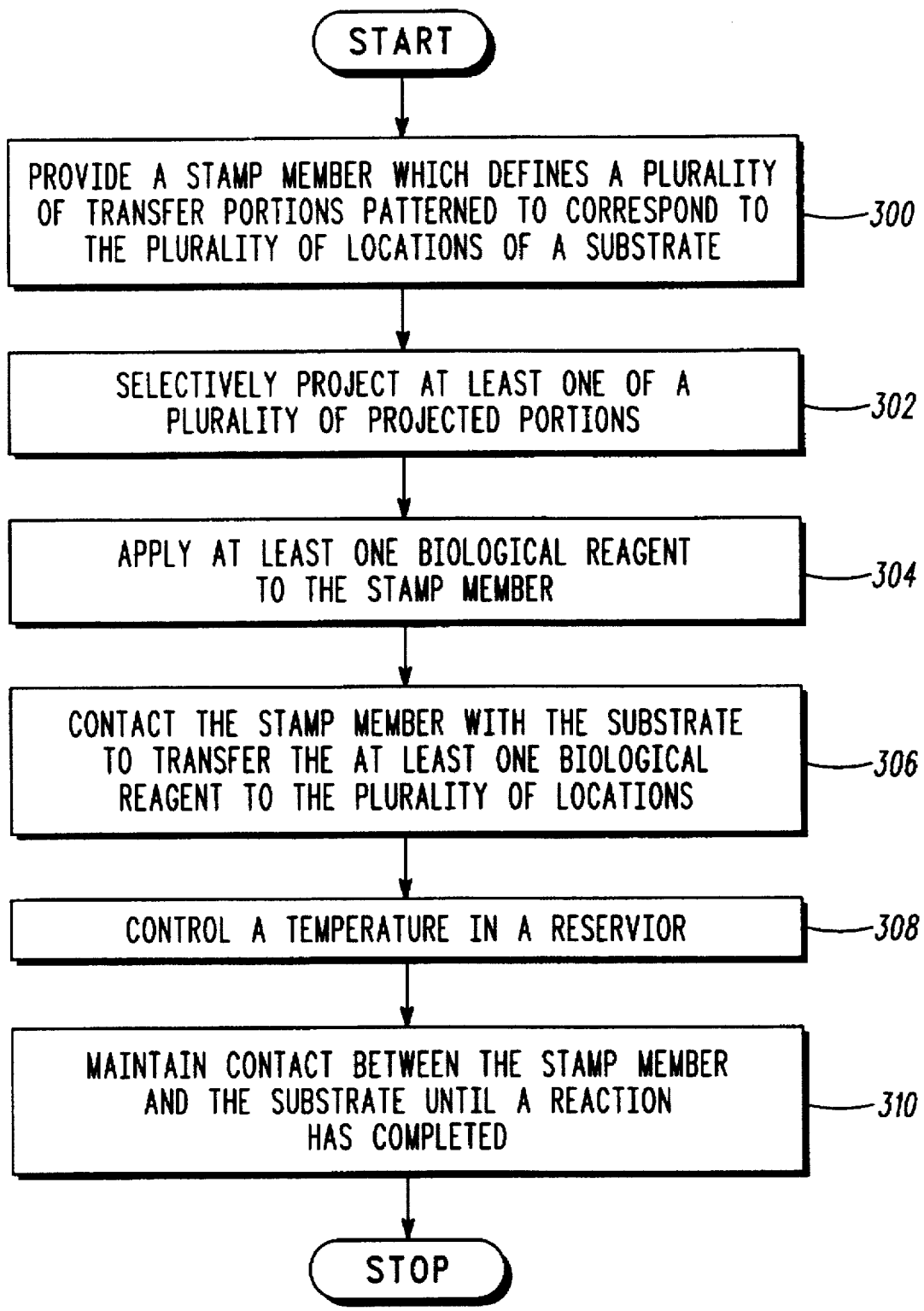
FIG. 19 is a flow chart summarizing steps performed in an embodiment of method of placing at least one biological reagent at a plurality of locations on a substrate.

FIG. 19 is a flow chart summarizing steps performed in an embodiment of method of placing at least one biological reagent at a plurality of locations on a substrate. As indicated by block 300, the method includes a step of providing a stamp member which defines a plurality of transfer elements patterned to correspond to the plurality of locations. Preferably, the stamp member is provided in accordance with those described herein, although alternative embodiments of the method are not limited thereto.

If the plurality of transfer elements have the form of a plurality of projected portions of the stamp member, an optional step of selectively projecting at least one of the plurality of projected portions can be performed, as indicated by block 302. Each of the at least one of the plurality of projected portions can be electromechanically projected by a respective piston in the stamp member as described earlier. However, other means for selective projecting the at least one of the plurality of projected portions can also be utilized.

As indicated by block 304, a step of applying the at least one biological reagent to the stamp member is performed. For a transfer element which includes a reservoir, this step can include applying a biological reagent to the reservoir by a capillary embedded in the stamp member. For a plurality of reservoirs, this step can include applying a respective biological reagent to each of the plurality of reservoirs by a respective one of a plurality of capillaries embedded in the stamp member.

As indicated by block 306, a step of contacting the stamp member with the substrate is performed to transfer the at least one biological reagent from the plurality of transfer elements to the plurality of locations. As described earlier, the step of contacting the stamp member with the substrate can include either stamping or rolling the stamp member onto the substrate.

As indicated by block 308, an optional step of controlling a temperature in a reservoir can be performed. This step can include applying a signal to a heating element in the stamp member proximate to the reservoir. The temperature can be controlled in this step to control a reaction which occurs in the reservoir.

As indicated by block 310, a step of maintaining contact between the stamp member and the substrate can be performed until a reaction involving the at least one biological reagent has completed. Thereafter, the stamp member is removed from the substrate.

As described earlier, this method is particularly advantageous where the at least one biological reagent includes at least one nucleotide, and where the plurality of locations are binding sites in a molecular detection apparatus.

Thus, there has been described herein a concept, as well as several embodiments including preferred embodiments of methods and systems for biological reagent placement.

Because the various embodiments of the present invention utilize a stamp member which transfers a reagent by contacting a substrate, they provide a significant improvement in that photolithographic patterning is not required to define chemically active areas on the substrate. This can increase yield of a multilevel fabrication process by reducing a number of steps involved. Further, the stamping process is scalable to large areas and compatible with high-throughput manufacturing requirements.

The use of reservoirs as transfer elements reduces an amount of reagent needed in comparison to immersing the entire substrate into a solution. The use of selectively projectable pistons to define the transfer elements is advantageous in that the stamp member can be reconfigured in real-time.

Additionally, the various embodiments of the present invention as herein-described allow chemical reactions, including hybridization, to be accurately controlled by including providing temperature control at each of the transfer elements. This reduces a requirement of uniform temperature across an entire substrate.

Further, the various embodiments of the present invention allow different samples to be placed only at predetermined regions on a substrate, such as a molecular detection chip. Limiting sample placement can reduce a likelihood of false-positive hybridization (or partial hybridization) in comparison to applying a sample to all of a plurality of combinatorial sites on a molecular detection chip.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A method of placing at least one biological reagent at a plurality of locations on a substrate, the method comprising the steps of:

providing a stamp member having a plurality of projected portions, each of the projected portions having at least one cavity therein;

applying the at least one biological reagent to the stamp member; and contacting the stamp member with the substrate to transfer the at least one biological reagent from the stamp member to the plurality of locations.

2. The method of claim 1 wherein the stamp member is cylindrically-shaped.

3. The method of claim 2 wherein the step of contacting the stamp member with the substrate includes rolling the stamp member onto the substrate.

4. The method of claim 1 wherein the at least one biological reagent includes at least one nucleotide.

5. The method of claim 1 wherein the plurality of locations include a plurality of binding sites.

6. The method of claim 1 wherein the plurality of projected portions absorb the at least one biological reagent when the at least one biological reagent is applied to the stamp member.

7. The method of claim 6 wherein the plurality of projected portions are made from an absorbent material.

8. The method of claim 7 wherein the stamp member includes a support member which supports the absorbent material.

9. The method of claim 1 wherein the stamp member has a capillary disposed therein.

10. The method of claim 1 wherein the at least one biological reagent is applied to each of the plurality of projected portions.

11. The method of claim 10 wherein the common biological reagent is applied to the stamp member by a roller.

12. The method of claim 1 further comprising the step of selectively further projecting at least one of the plurality of projected portions.

13. The method of claim 12 wherein the at least one of the plurality of projected portions is electromechanically projected.

14. The method of claim 13 wherein each of the at least one of the plurality of projected portions is electromechanically extended by a respective piston in the stamp member.

15. The method of claim 14 wherein the stamp member includes an absorbent layer which is deformable by each respective piston.

16. A method of placing at least one biological reagent at a plurality of locations on a substrate, the method comprising the steps of:
providing a stamp member having a surface with a plurality of reservoirs disposed therein;
applying the at least one biological reagent to the stamp member; and
contacting the stamp member with the substrate to transfer the at least one biological reagent from the stamp member to the plurality of locations.

17. The method of claim 16 further comprising the step of maintaining contact between the stamp member and the substrate until a reaction which involves the at least one biological reagent has completed.

18. The method of claim 17 wherein the reaction includes a hybridization event.

19. The method of claim 16 wherein the stamp member includes a plurality of capillaries.

20. An apparatus for placing at least one biological reagent at a plurality of locations on a substrate, the apparatus comprising:
a stamp member onto which the at least one biological reagent is applied, the stamp member having a plurality of projections, each of the projected portions having at least one cavity, the stamp member for contacting with the substrate to transfer the at least one biological reagent to the plurality of locations.

21. The apparatus of claim 20 wherein the stamp member is cylindrically-shaped.

22. The apparatus of claim 21 wherein the stamp member is rolled onto the substrate to transfer the at least one biological reagent to the plurality of locations.

23. The apparatus of claim 20 wherein the stamp member has a surface with a plurality of reservoirs therein.

24. The apparatus of claim 23 wherein the at least one biological reagent includes at least one nucleotide.

25. The apparatus of claim 23 wherein the plurality of locations are binding sites in a molecular detection apparatus.

26. The apparatus of claim 23 wherein the plurality of projected portions absorb the at least one biological reagent when the at least one biological reagent is applied to the stamp member.

27. The apparatus of claim 26 wherein the stamp member includes an absorbent layer which includes the plurality of projected portions.

28. The apparatus of claim 27 wherein the stamp member includes a support member which supports the absorbent layer.

29. The apparatus of claim 23 further comprising a capillary embedded in the stamp member.

30. The apparatus of claim 23 wherein the at least one biological reagent is applied to each of the plurality of projected portions.

31. The apparatus of claim 23 further comprising means for selectively further projecting at least one of the plurality of projected portions.

32. The apparatus of claim 31 wherein the at least one of the plurality of projected portions is electromechanically projected.

33. The apparatus of claim 32 wherein the means for selectively further projecting the at least one of the plurality of projected portions includes a piston in the stamp member.

34. The apparatus of claim 33 wherein the stamp member includes an absorbent layer which is deformed by the piston.

35. All apparatus for placing at least one biological reagent at a plurality of locations on a substrate, the apparatus comprising:
a stamp member having a biological reagant application surface with a plurality of reservoirs disposed therein and a plurality of capillaries embedded into the stamp member.

36. The apparatus of claim 35 wherein contact is maintained between the stamp member and the substrate until a reaction which involves the at least one biological reagent has completed.

37. The apparatus of claim 36 wherein the reaction includes a hybridization event.

38. The apparatus of claim 35 wherein the plurality of locations are binding sites in a molecular detection apparatus.

39. A method of placing at least one biological reagent onto a substrate, the method comprising the steps of:
providing a stamp member having a plurality of projected portions, each of the projected portions having at least one cavity therein;
applying the at least one biological reagent to the stamp member using a roller, and
transferring the at least one biological reagent from the stamp member to the substrate.

40. A method of placing at least one biological reagent onto a substrate, the method comprising the steps of:
providing a stamp member having a surface with a plurality of reservoirs disposed therein;

applying the at least one biological reagent to the stamp member using a roller, and transferring the at least one biological reagent from the stamp member to the substrate.

41. An apparatus for placing at least one biological reagent at a plurality of locations on a substrate, the apparatus comprising:

a stamp member having plurality of projected portions on a cylindrical surface each projected portion having at least one cavity therein, said plurality of projected portions capable of transferring the at least one biological reagent to a plurality of locations.

42. The apparatus of claim 41 wherein the cylindrical surface is rolled on the substrate to transfer the at least one biological reagent to the substrate.

43. A method of placing at least one biological reagent at a plurality of locations on a substrate, the method comprising the steps of:

providing a stamp member having a plurality of projected portions on a cylindrical surface;

applying the at least one biological reagent to the plurality of projected portions; and transferring the at least one biological reagent from the plurality of projected portions to the substrate.

44. The method of claim 43 wherein the step of transferring includes rolling the cylindrical surface on the substrate.

* * * * *

UNITED STATES PATENT AND TRADEMARK OFFICE
CERTIFICATE OF CORRECTION

PATENT NO. : 5,731,152
DATED : March 24, 1998
INVENTOR(S) : Maracas et al.

It is certified that error appears in the above-indentified patent and that said Letters Patent is hereby corrected as shown below:

Claim 35, Line 1, "All" should be --An--

Signed and Sealed this

Twenty-seventh Day of July, 1999

Attest:

Q. TODD DICKINSON

*Attesting Officer*   Acting Commissioner of Patents and Trademarks